United States Patent [19]
Carilli

[11] Patent Number: 5,709,667
[45] Date of Patent: Jan. 20, 1998

[54] HYPODERMIC NEEDLE PROTECTION SYSTEM

[76] Inventor: Brian D. Carilli, 2150 Columbia St., Palo Alto, Calif. 94306

[21] Appl. No.: 443,120

[22] Filed: May 17, 1995

[51] Int. Cl.$^6$ .................................................. A61M 5/32
[52] U.S. Cl. .................. 604/198; 604/110; 604/192; 604/187; 604/240
[58] Field of Search .................................. 604/110, 192, 604/195, 198, 187, 239, 240, 255, 263, 272

[56] References Cited

U.S. PATENT DOCUMENTS

| | | | |
|---|---|---|---|
| 3,306,290 | 2/1967 | Weltman | 128/218 |
| 4,139,009 | 2/1979 | Alvarez | 128/218 |
| 4,493,703 | 1/1985 | Butterfield | 604/110 |
| 4,507,117 | 3/1985 | Vining et al. | 604/196 |
| 4,573,976 | 3/1986 | Sampson et al. | 604/198 |
| 4,767,413 | 8/1988 | Haber et al. | 604/198 |
| 4,790,822 | 12/1988 | Haining | 604/110 |
| 4,801,295 | 1/1989 | Spencer | 604/198 |
| 4,804,372 | 2/1989 | Laico et al. | 604/198 |
| 4,813,426 | 3/1989 | Haber et al. | 128/763 |
| 4,820,275 | 4/1989 | Haber et al. | 604/198 |
| 4,832,696 | 5/1989 | Luther et al. | 604/164 |
| 4,838,869 | 6/1989 | Allard | 604/195 |
| 4,846,808 | 7/1989 | Haber et al. | 604/195 |
| 4,892,521 | 1/1990 | Laico et al. | 604/192 |
| 4,900,311 | 2/1990 | Stern et al. | 604/198 |
| 4,908,022 | 3/1990 | Haber | 604/195 |
| 4,909,794 | 3/1990 | Haber et al. | 604/195 |
| 4,921,486 | 5/1990 | DeChellis et al. | 604/110 |
| 4,927,018 | 5/1990 | Yang et al. | 206/365 |
| 4,935,014 | 6/1990 | Haber | 604/195 |
| 4,935,015 | 6/1990 | Hall | 604/195 |
| 4,946,446 | 8/1990 | Vadher | 604/198 |
| 4,950,241 | 8/1990 | Ranford | 604/110 |
| 4,950,251 | 8/1990 | Haining | 604/195 |
| 4,950,252 | 8/1990 | Luther et al. | 604/198 |
| 4,955,870 | 9/1990 | Ridderheim et al. | 604/195 |
| 4,966,592 | 10/1990 | Burns et al. | 604/198 |
| 4,966,593 | 10/1990 | Lennox | 604/198 |
| 4,973,316 | 11/1990 | Dysarz | 604/195 |
| 4,978,340 | 12/1990 | Terrill et al. | 604/195 |
| 4,978,343 | 12/1990 | Dysarz et al. | 604/195 |
| 4,986,813 | 1/1991 | Blake, III et al. | 604/110 |
| 4,988,339 | 1/1991 | Vadher | 604/197 |
| 4,998,922 | 3/1991 | Kuracina et al. | 604/192 |
| 5,015,240 | 5/1991 | Soproni et al. | 604/192 |
| 5,049,136 | 9/1991 | Johnson | 604/198 |
| 5,053,010 | 10/1991 | McGary et al. | 604/110 |
| 5,088,986 | 2/1992 | Nusbaum | 604/195 |
| 5,092,853 | 3/1992 | Couvertier, II et al. | 604/195 |
| 5,098,401 | 3/1992 | DeLange | 604/192 |
| 5,098,402 | 3/1992 | Davis | 604/195 |
| 5,151,089 | 9/1992 | Kirk, III et al. | 604/192 |
| 5,163,907 | 11/1992 | Szuszkiewicz | 604/110 |
| 5,163,917 | 11/1992 | Huefner et al. | 604/198 |
| 5,171,300 | 12/1992 | Blake, III et al. | 604/110 |
| 5,180,370 | 1/1993 | Gillespie | 604/110 |
| 5,188,599 | 2/1993 | Botich et al. | 604/110 |
| 5,221,262 | 6/1993 | Kite | 604/110 |

(List continued on next page.)

*Primary Examiner*—Corrine M. McDermott
*Assistant Examiner*—Cris L. Rodriguez
*Attorney, Agent, or Firm*—Flehr, Hohbach, Test, Albritton and Herbert LLP

[57] ABSTRACT

A hypodermic needle assembly for use with an injection device. The needle assembly includes a sheath having a front end and a recess extending inwardly from the front end of the sheath, and a needle carriage positioned in the sheath. A needle is mounted to the carriage. The needle carriage is movable along the recess between a forward position with the needle projecting from the front end of the sheath and a retracted position with the needle positioned inside of the sheath. The sheath has a plurality of first locking members and the needle carriage has at least one second locking member cooperable with the first locking members for selectively retaining the needle carriage in each of the forward position and the retracted position when the second locking member and one of the first locking members are engaged and for moving the needle carriage relative to the sheath when the second locking member and the first locking members are disengaged.

13 Claims, 6 Drawing Sheets

U.S. PATENT DOCUMENTS

| | | | |
|---|---|---|---|
| 5,222,944 | 6/1993 | Harris | 604/110 |
| 5,226,893 | 7/1993 | Kayser | 604/195 |
| 5,242,400 | 9/1993 | Blake, III et al. | 604/110 |
| 5,250,031 | 10/1993 | Kaplan et al. | 604/110 |
| 5,263,942 | 11/1993 | Smedley et al. | 604/195 |
| 5,267,961 | 12/1993 | Shaw | 604/110 |
| 5,269,766 | 12/1993 | Haber et al. | 604/198 |
| 5,279,582 | 1/1994 | Davison et al. | 604/198 |
| 5,279,583 | 1/1994 | Shober, Jr. et al. | 604/198 |
| 5,290,233 | 3/1994 | Campbell | 604/110 |
| 5,300,038 | 4/1994 | Haber et al. | 604/187 |
| 5,304,150 | 4/1994 | Duplan et al. | 604/195 |
| 5,318,536 | 6/1994 | Williams | 604/110 |
| 5,330,430 | 7/1994 | Sullivan | 604/134 |
| 5,336,198 | 8/1994 | Silver et al. | 604/195 |
| 5,338,311 | 8/1994 | Mahurkar | 604/195 |
| 5,342,323 | 8/1994 | Haining | 604/195 |
| 5,342,324 | 8/1994 | Tucker | 604/264 |
| 5,344,403 | 9/1994 | Lee | 604/110 |
| 5,346,480 | 9/1994 | Hess et al. | 604/197 |
| 5,360,409 | 11/1994 | Boyd, III et al. | 604/198 |
| 5,374,250 | 12/1994 | Dixon | 604/110 |
| 5,378,240 | 1/1995 | Curie et al. | 604/110 |
| 5,393,301 | 2/1995 | Goldberg | 604/110 |
| 5,401,246 | 3/1995 | Mazur et al. | 604/110 |
| 5,498,245 | 3/1996 | Whisson | 604/198 |
| 5,520,654 | 5/1996 | Wahlberg | 604/164 |

HYPODERMIC NEEDLE PROTECTION SYSTEM

BACKGROUND OF THE INVENTION

The present invention relates to the field of safety devices for hypodermic needles, and in particular to a side-mounted system for a hypodermic needle allowing for the needle to be retracted after use.

The hypodermic needle is one of the most useful and common tools in modern medicine, but it is also one of the most dangerous. Common microorganisms, including deadly viruses, are known to be communicable through infected hypodermic needles. In the urgent environment of ambulances or hospital emergency rooms, used and exposed hypodermic needles present a hazard to medical workers or patients. An accidental stab or scratch produced by such needles can introduce dangerous viruses or other contaminants directly into a person's blood stream. Therefore, there is a need for protecting medical personnel and patients from exposed hypodermic needles.

Many solutions have been proposed to solve the problem. Most involve very complex, spring-loaded mechanisms for automatic needle retraction after injection. These are unsuitable for disposable syringes because of cost considerations. In addition, their intricate construction increases the chances of malfunctioning.

Another group of solutions proposes a manual retraction systems. These tend to be very inconvenient and cumbersome to operate. The number of steps to be performed by the person administering an injection is drastically increased. In addition, manual retraction systems, as well as the automatic ones referred to above, increase the number of parts on the front of the syringe barrel. This limits the range of angles from which the needle can be introduced under the patient's skin. In fact, with all the fixtures and attachments required for safe needle retraction, the operator is restricted to a ninety degree angle of entry. Under this angle the needle penetrates deep under the patient's skin and is frequently hard to withdraw.

Of course, the advantage of a shallower angle of entry has been recognized in the art. Many old-fashioned syringes have a needle-mounting snout located off-center for this very reason. Nonetheless, for technical reasons having to do with the retraction mechanism, no state of the an solution incorporates the concept of shallow entry angle and protection of the hypodermic needle.

OBJECTS AND SUMMARY OF THE INVENTION

Therefore, it is an object of the invention to provide an automatic, reliable means for a hypodermic needle to be retracted into a protective housing after being used, and to prevent the needle from leaving the housing henceforth without an explicit and intentional motion by the user of the needle.

It is another object of the invention to ensure that the hypodermic needle guard is simple in construction, made with commonly available components, inexpensive, easy to install, and reliable. In particular, it is an object of the invention to prevent the needle from accidentally protruding once it is inside the needle guard. In addition, it is another object of the invention to allow the needle to be permanently withdrawn into the housing once it has been used, to ensure that the needle never protrudes again before it is disposed of. Furthermore, it is another object of the invention to allow a needle to be retracted into an area immediately adjacent to the body of a syringe, where it stands very little chance of accidentally protruding from its housing.

It is yet another object of the invention to allow a hypodermic needle to be inserted into a subject's skin at a substantially small angle of entry with respect to the skin.

These and other objects and advantages will become more apparent after consideration of the ensuing description and the accompanying drawings.

The invention combines the innovation of mounting a hypodermic needle on one side of a syringe, rather than in the center, with the idea of encasing or removing the needle after it has been used. Therefore, one embodiment of this invention teaches that a needle mounted on a carriage can slide within a sheath, where this sheath is mounted on the side of a syringe or other chamber filled with fluid. The needle can slide to one of three positions; in the first position, it is closest to the front of the syringe, and it is ready to be used. In this position, the carriage mounted to the needle is in the right position to trigger the chamber to open a side outlet and allow fluid to pass through the outlet, through a duct in the carriage, and out through the needle. In the second position, the outlet is closed, and the needle and carriage are reversibly retracted into the sheath. In a third position, the outlet is also closed, and the needle and carriage are retracted, even deeper into the sheath, irreversibly, so that the needle can not be made to protrude. This is the disposal position. In the most preferred embodiment the carriage and needle are locked into these three positions along a sliding track by means of flexible legs on the carriage which protrude into notches on the track. The operator frees the carriage and needle from these notches by depressing buttons to compress the legs.

In other embodiments, this invention teaches that the entire sheath containing the carriage and needle can be removed from the chamber of fluid. Alternatively, the carriage and needle unit may be removable from the sheath. Both of these variations use reversible mounting mechanisms, such as mechanical snapping-on of parts. In another embodiment, this invention teaches that the sheath is unnecessary; only the carriage and needle need to be removably mounted onto the chamber, so that once the needle has been used, it can be removed easily and safely from the chamber.

DESCRIPTION OF THE PREFERRED EMBODIMENTS

Reference will now be made in detail to the preferred embodiment of the invention, which is illustrated in the accompanying figures. Turning now to the drawings, wherein like components are designated by like reference numerals throughout the various figures, attention is directed to FIGS. 1–6.

Figure 1:
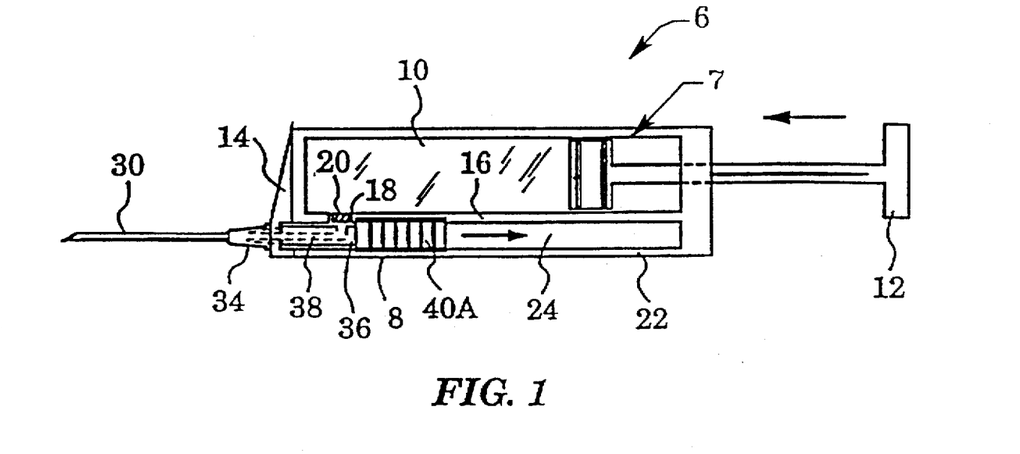
FIG. 1 is a side view of the preferred embodiment of the invention.

FIGS. 1–6 show an embodiment of a hypodermic needle protection system 6 in accordance with the present invention. The needle protection system 6 generally includes a syringe body 7 and a needle assembly 8 having a needle 30 which may be easily moved from the extended position shown in FIG. 1 to a retracted position with the contaminated needle safely contained within a protective sheath 22. As is shown in FIG. 1, the syringe body 7 and needle assembly 8 are formed as a single unit. After the used needle 30 has been retracted within the sheath 22, the entire unit may be safely discarded. In alternative forms of the invention, such as those shown in FIGS. 8–11, the syringe body 7 and needle assembly 8 may be separate components with the needle assembly being detachable from the syringe body for disposal of the needle. Providing the needle assembly 8 as a separate component is particularly useful when the hypodermic needle is used to extract a sample of fluid, such as blood, from the patient's body.

Turning particularly to FIG. 1, syringe body 7 includes a chamber 10 and a plunger 12 extending through the chamber 10. The chamber 10 is filled with injection fluid, although in applications where the hypodermic is used to collect fluid the chamber 10 may be empty. Near the front end 14 of chamber 10, within a side wall 16, there is an outlet 18. A valve, such as a check valve 20, is fixed in outlet 18 to control the flow of fluid through outlet 18. The chamber 10 has a central axis substantially aligned with the plunger 12.

The sheath 22 of the needle assembly 8 is positioned to one side of the chamber 10, with the central axis of the sheath offset from the central axis of the chamber With this configuration, the syringe body 7 will not interfere with the orientation of the needle relative to the patient's body, allowing the needle to be inserted into the skin at a substantially small angle. In addition, this configuration is particularly suitable for embodiments of the invention in which the sheath is detachable from the chamber Although positioning the needle assembly 8 to one side of the syringe body 7 is preferred, it should be understood that in other modifications of the invention the syringe body 7 may extend circumferentially around a major portion of the needle assembly 8 if desired. In the present embodiment, the sheath 22 is defined by the side wall 16 of the chamber 10 and an two spaced flanges or side wall depending from the side wall 16 and having a lower edge opposite the side wall 16 of the chamber. The flanges form a U-shaped channel or recess 24 which defines an interior passageway of the sheath 22. Alternatively, the sheath may include a bottom wall spaced from the side wall 16 of the chamber. Depending upon the length of the chamber 10 and the size of the needle 30, the recess 24 may extend along the entire length of the chamber as shown in FIG. 1 or the recess 24 may be shorter or longer than the chamber. In the embodiment shown in FIGS. 1–6, the sheath 22 is permanently mounted to or integrally or monolithically formed with the chamber In other embodiments of the invention, the sheath 22 may be removably mounted to the chamber 10.

A carriage 36 mounted within recess 24 may be moved from one end of recess 24 to the other. The needle 30 is attached at the front end of carriage 36. The carriage preferably includes a conduit for delivering fluid to the needle 30. In the embodiment shown in FIG. 1, carriage 36 has a duct 38 which extends from the valve 20 to the needle 30, presenting the only path for fluid to flow between chamber 10 and needle 30. Two actuators or buttons 40A and 40B are provided on either side of the carriage 36 for controlling the position of carriage 36. They extend outside recess 24, with the stems of the actuator buttons engaging two lateral slots 26 formed in the walls of sheath 22. Lateral slots 26 extend along the length of recess 24 and end before reaching the front end of recess 24. The carriage 36 may be moved along the recess 24 by sliding the actuators 40A and 40B along the slots 26. The front ends of the slots 26 prevent the carriage from falling out of recess 24.

Figure 2:
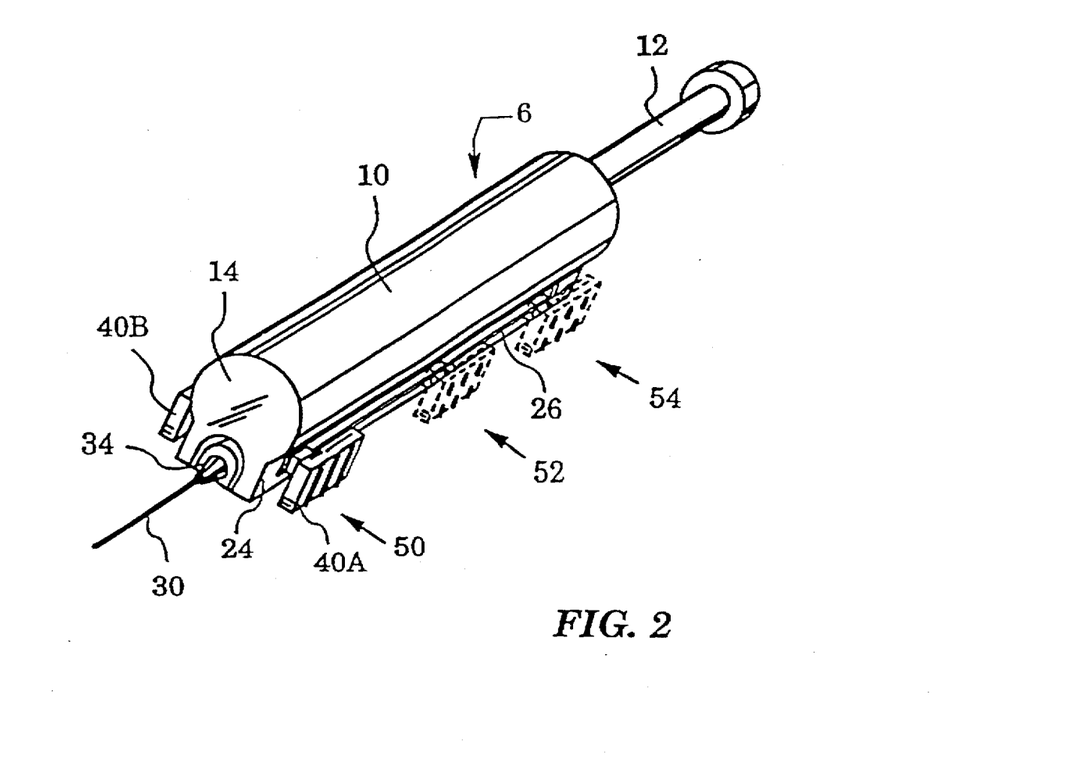
FIG. 2 is a perspective view of the embodiment of FIG. 1, showing three states for the needle.

As is shown in FIG. 2, the carriage 36 may be moved within recess 24 between three positions. In a ready-position 50, carriage is near the front end 14 of chamber 10. Duct 38 is aligned with the chamber outlet 18 (FIG. 1) and positioned to open valve 20 (FIG. 1), allowing fluid to flow from the chamber 10 to needle 30. In the standby-position 52, carriage 36 and needle 30 are completely retracted into recess 24, protecting the needle 30 against contamination. With the carriage 36 in the stand-by position, the needle 30 is positioned within the sheath 22 for the safe storage and handling of the unused device. However, in other forms of the invention the needle 30 may be supplied in the extended position shown in FIG. 1 with a removable sleeve covering and protecting the needle prior to use as is known in the art. As is described in more detail below, the carriage may be easily moved from the stand-by position 52 to the ready-position 50. After the needle 30 has been used, the carriage 36 may be retracted to the disposal-position 54. Unlike the stand-by position 52, the carriage 36 may not be moved forwardly from the disposal position 54 to either the stand-by position 52 or the ready position 50.

Figures 3, 4:
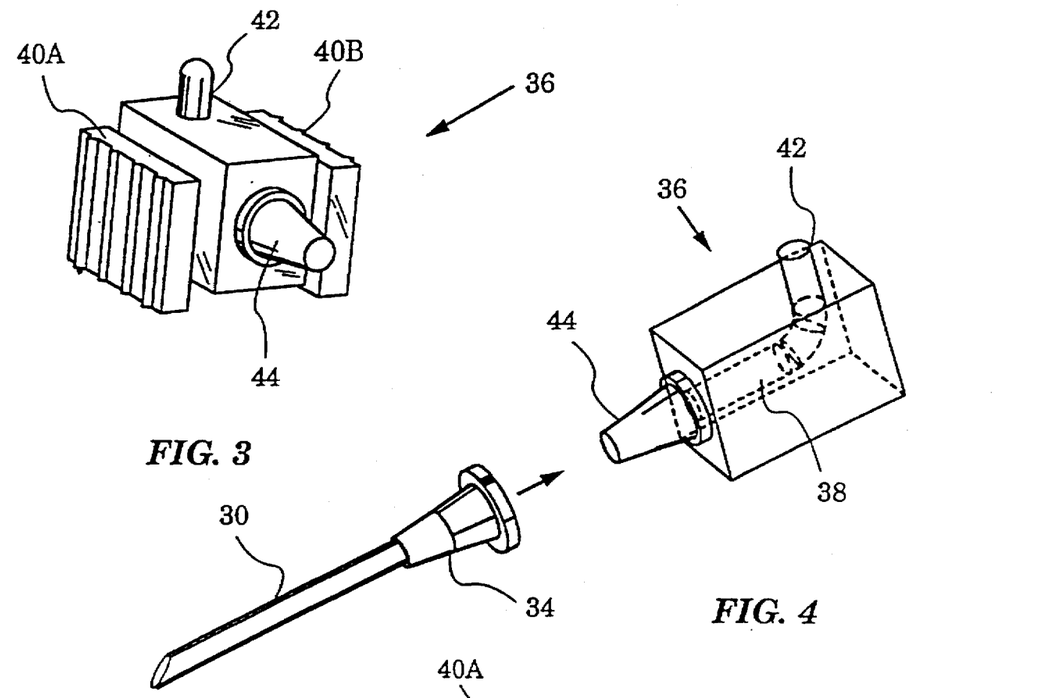
FIG. 3 is a perspective view of a part of the embodiment of FIG. 1, the carriage containing the needle.
FIG. 4 is a perspective view of how the needle in the embodiment of FIG. 1 is attached to the needle carriage.

FIGS. 3 and 4 show a more detailed view of carriage 36. Actuators 40A and 40B jut out from either side of the carriage. On the upper surface of carriage 36 facing chamber 10, duct 38 ends in a dome-shaped distal end 42 formed to open the valve 20 and permit discharge of the fluid from the chamber 36. A nose-shaped connector 44 coupled to the proximal end of the duct 38 projects from the front end of the carriage 36. Needle 30 has a receptor 34 on its end which attaches firmly to connector 44. In this embodiment, connector 44 is a regular tube for snapping on hypodermic needles by their receptor 34. This snap-on mechanism is well-known in the art.

Figure 5:
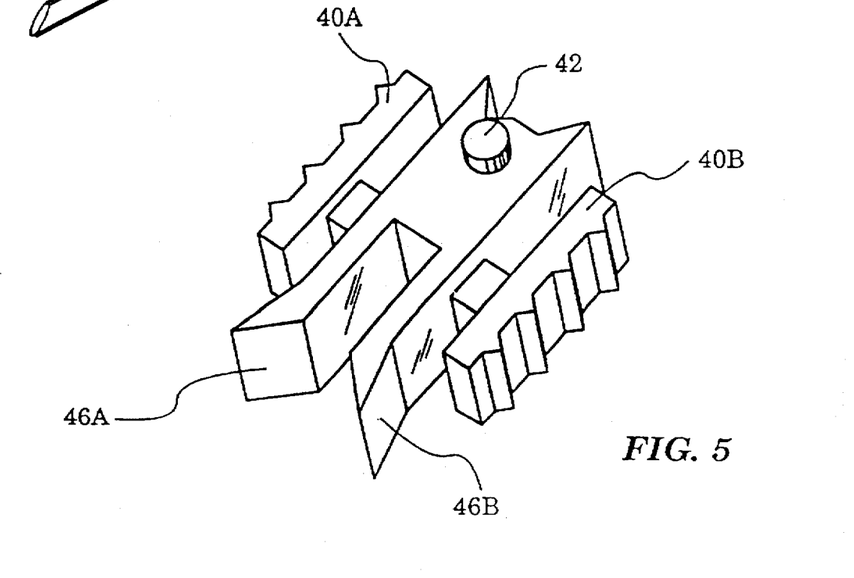
FIG. 5 is a perspective view of the locking legs of the carriage of the embodiment of FIG. 1.

FIG. 5 shows the locking feature of carriage 36 which secures the carriage 36 in each of the positions 50, 52 and 54 shown in FIG. 2. Two elastic legs 46A and 46B extend outwardly from the back end of the carriage 36. Legs 46A and 46B are tapered, and jut out slightly beyond the width of carriage 36. Actuators 40A and 40B are attached to legs 46A and 46B in such a way that when button 40A is depressed, leg 46A bends inward, so that it no longer juts outward, and button 40B depresses leg 46B in a similar way. Of course, there are many other mechanical solutions for a locking mechanism adaptable to carriage 36. Corresponding grooves, notches, catches and other provisions for actuating such locking mechanisms can be easily incorporated on the side of the syringe or inside sheath 22.

Figure 6:
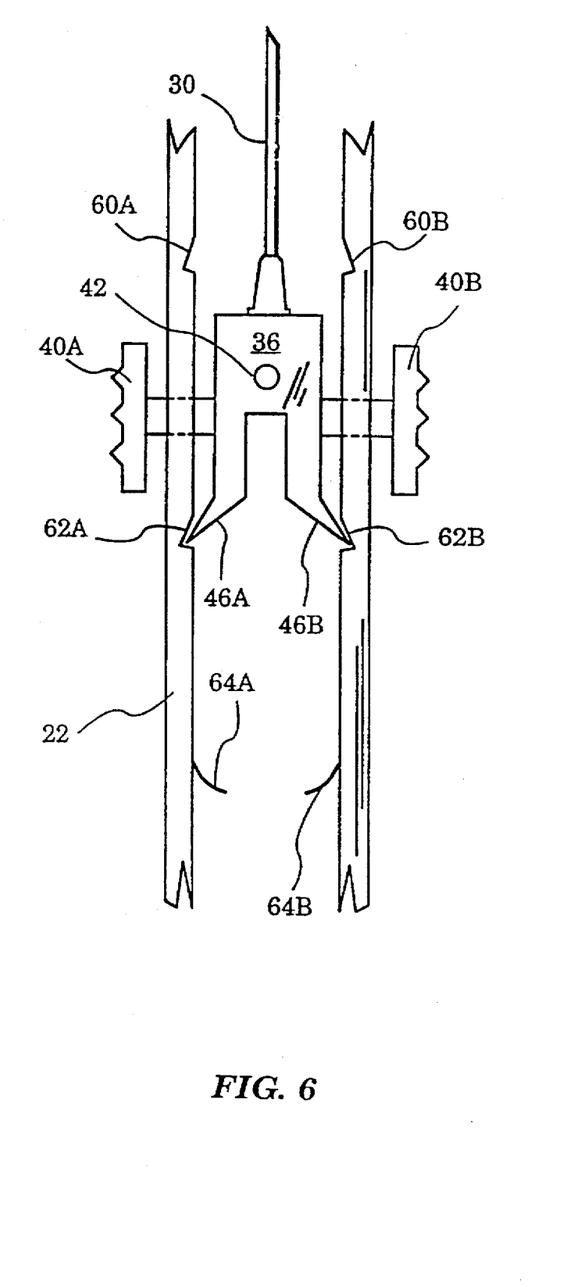
FIG. 6 is a cross-section view of the entire locking mechanism of the embodiment of FIG. 1.

The operation of the locking mechanism is shown in FIG. 6. The walls of the recess 24 are formed with a plurality of notches shaped to engage the legs 46A and 46B of the carriage 36 and retain the carriage in one of the positions 50 and 52. The first two notches, which are the ready-position notches 60A and 60B, are closer to front end (shown in FIGS. 1 and 2) 14. When the legs 46A and 46B engage the notches 60A and 60B, the carriage 36 is held securely in the ready position 50. The engagement between the legs and the notches prevents the carriage 36 from moving backwards, withstanding the force required to insert the needle into the patient's body. Once needle 30 has been used, actuators 40A and 40B are pressed together to disengage the legs 46A and 46B from the notches 60A and 60B and the carriage 36 may be moved backwards. The notches 62A and 62B engage the legs 46A and 46B to retain the carriage 36 in the standby-position, preventing forward and backward movement of the carriage until the actuators 40A and 40B are depressed. When the operator moves carriage 36 backwards to disposal-position 54, (shown in FIG. 2) the legs 46A and 46B are moved past two tabs 64A and 64B which catch carriage 36 and prevent it from moving forwards again. In this embodiment, the tabs are leaf springs. However, the configuration of the tabs are subject to considerable variation. Because sheath 22 is closed at the back end, carriage 36 is thereby fixed in position; there is no mechanism for moving it either forwards or backwards. However, in other embodiments of the invention the sheath may be open at its back end to allow carriage 36 and needle 30 to be removed from the recess 24.

Figure 7:
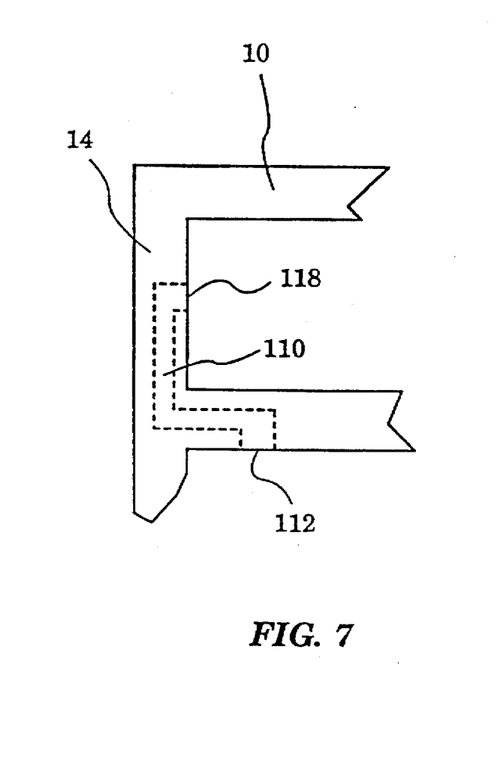
FIG. 7 is a side view of an alternative embodiment of the invention.

The outlet 18 and duct 38 provide a passageway for transporting fluid between the chamber 10 and the needle 30. In the embodiment shown in FIGS. 1–6, the chamber 10 is formed with an outlet which extends straight through the chamber wall. FIG. 7 shows an alternative embodiment of the chamber 10 in which the outlet 18 is replaced by a conduit 110 extending from an interior opening in the front wall of chamber 10 to an exterior opening on the side wall 16. With this embodiment, all the fluid held within chamber 10 may be injected into the patient's body. With the embodiment shown in FIGS. 1–6, the fluid between the front end 14 of the chamber and outlet 18 would become trapped within the chamber once the plunger 12 had passed outlet 18.

Figures 8, 9:
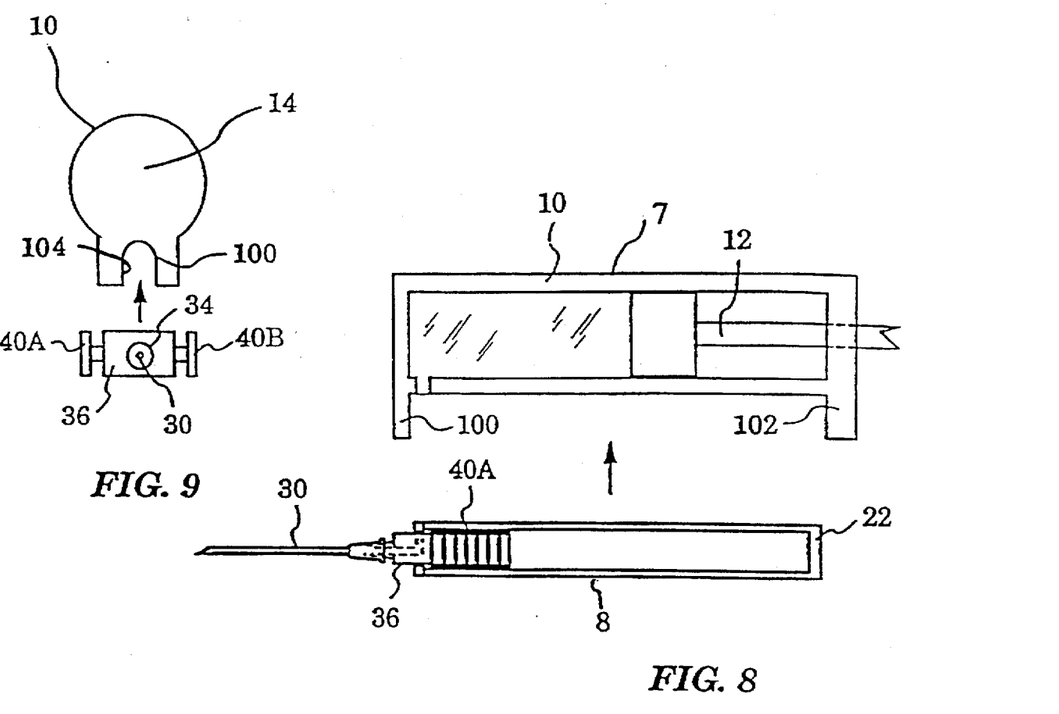
FIG. 8 is a side view of an alternative embodiment in which the sheath is removable from the syringe.
FIG. 9 is a frontal view of the embodiment of FIG. 8.

FIG. 8 shows an embodiment of the invention in which the needle assembly 8 is detachable from chamber 10. In this embodiment, needle assembly 8 includes a sheath 22 which is mounted onto chamber 10 by a secure mounting system which allows the operator to remove sheath 22 after needle 30 has been used and safely retracted within the sheath. As is shown in FIG. 8, chamber 10 has a front wall 100 and a back wall 102 which extend beyond the side wall of the chamber. The sheath 22 may be snapped into the space between the front and back walls 100 and 102. The sheath 22 may be easily detached from the chamber 10 by pulling the sheath from between the front and back walls. In other embodiments, other means may be used to removably or permanently couple the sheath to the chamber. For example, sheath 22 may be screwed on, twisted on, slid on, magnetically placed onto chamber 10, or permanently affixed by adhesive, ultrasonic welding, and the like instead of snapping the sheath 22 in place.

FIG. 9 shows a frontal view of the embodiment of FIG. 8. Front wall 100 has a mouth 104 which allows the needle 30 to project from the front wall 100. Preferably, the carriage 36 is prevented from passing through the mouth 104. However, if desired the front ends of slots 26 may be used to interrupt the forward progress of the carriage. In the present invention, the mouth 104 is generally U-shaped slot extending upwardly from the lower edge of the front wall 100. Alternatively, the mouth may be provided as an aperture formed in the front wall 100.

Figure 10:
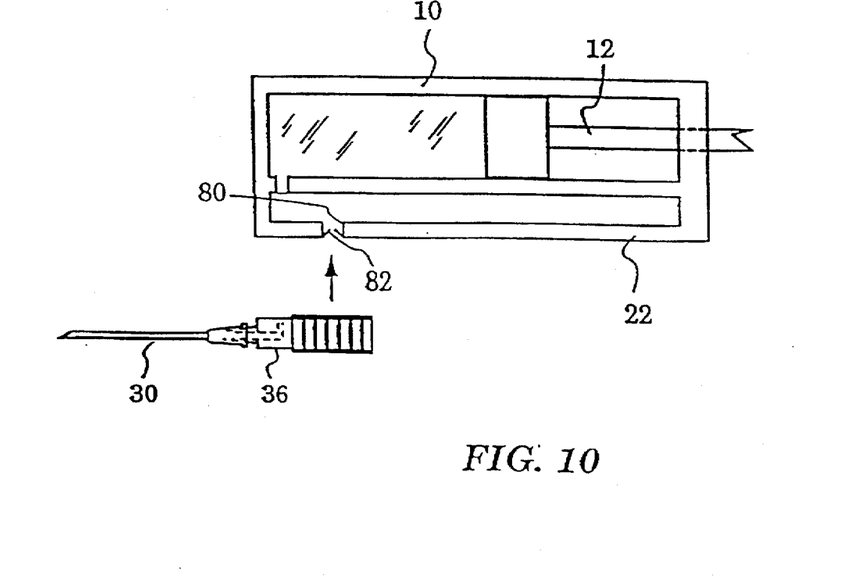
FIG. 10 is a side view of an alternative embodiment in which the carriage is removable from the sheath.

FIG. 10 shows another embodiment of the invention in which sheath 22 is integrally formed with or permanently mounted to the fluid chamber 10. The lower surface (not shown) of the sheath is open for insertion of the carriage 36 into the sheath 22. Sheath 22 has an opening 80 through which the stems of the actuator buttons may pass. Opening 80 has a pair of one-way keepers or tabs 82 which bend inward when the carriage 36 is inserted into the sheath. After the stems of the actuator buttons 40A and 40B pass through the opening 80, the keepers 82 return to their original shape and block carriage 36 from coming out of sheath 22 again. In this modification, the sheath 22 may consist of two spaced flanges depending from the chamber 10, with the engagement between the actuators 40A and 40B and the slots retaining the carriage 36 in the sheath. Alternatively, the sheath may have a bottom wall which is formed with an opening of sufficient size to receive carriage 36.

Figure 11:
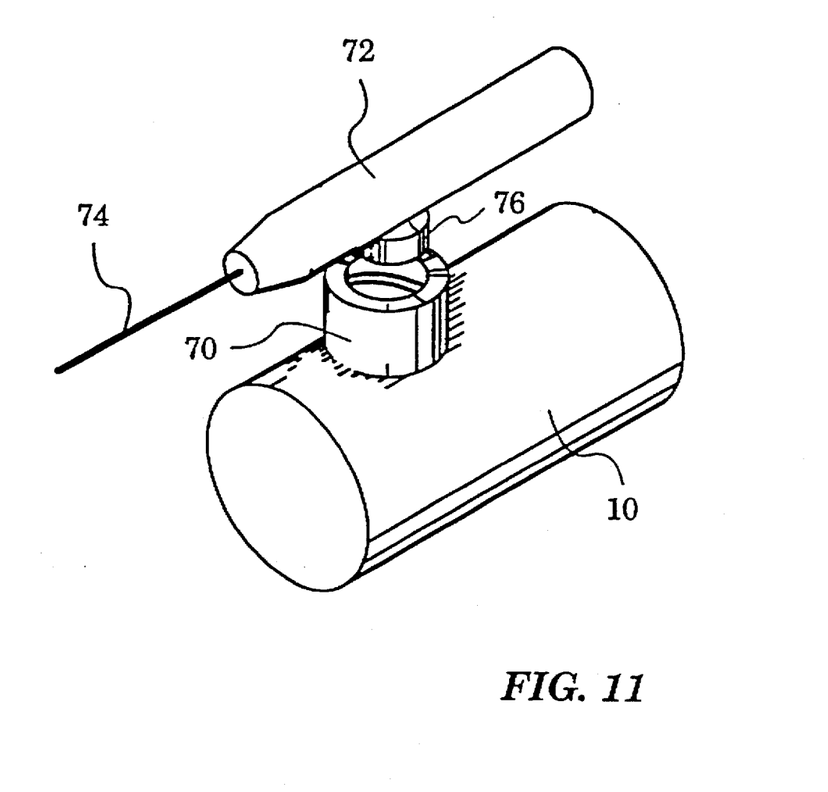
FIG. 11 is a perspective view of an alternative embodiment of the invention.
Figure 12:
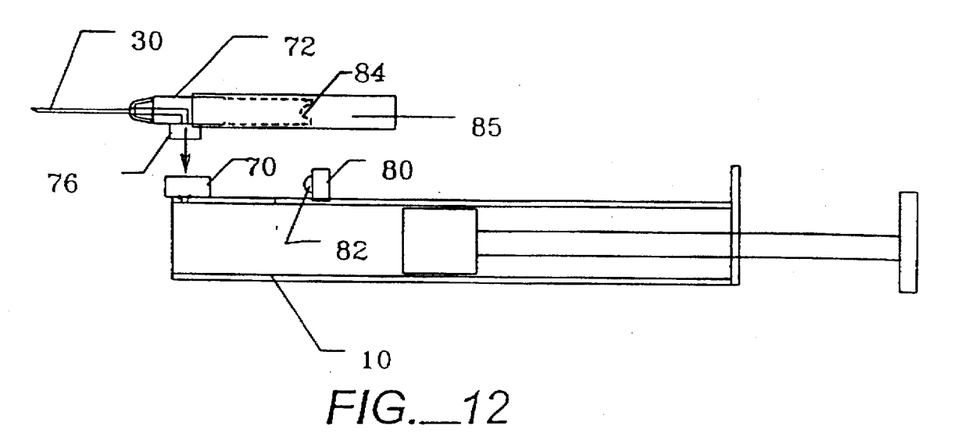
FIG. 12 is a top plan view of another embodiment of the invention.
Figure 13:
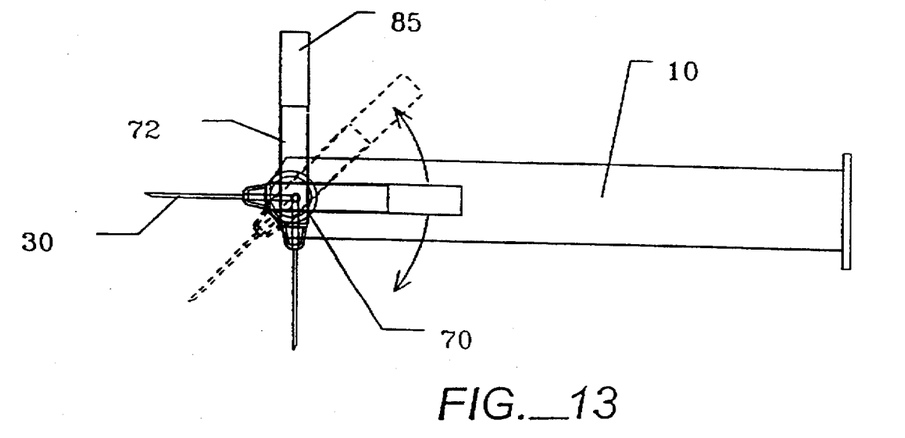
FIG. 13 is a top plan of another embodiment of the invention, shown with the needle oriented in a plurality of positions relative to the fluid chamber.

The advantages of positioning the needle 30 to the side of the fluid chamber 10 are further described in relation to the modifications shown in FIGS. 11–13. With these embodiments, the needle carriage may be efficiently mounted to the chamber 10 and removed from the chamber after the needle 30 has been used. A shallow angle of entry may be obtained by orienting the assembly with the needle carriage between the patient's skin and the chamber 10. As is described in relation to FIG. 13, the needle position is not restricted to a parallel orientation relative to the chamber 10.

In the modification shown in FIG. 11, carriage 72 does not slide along the syringe. Instead, the carriage 72 is mounted by screwing into the syringe. In this embodiment, chamber 10 has a socket 70 jutting out and surrounding outlet 18 (not shown). The spout 76 of carriage 72 securely engages the socket 70. In the present embodiment, the spout 76 and socket 70 are formed with screw threads which cooperate to securely retain the spout within the socket. However, various other means may be used to secure the carriage to the chamber 10 including, but not limited to, snap beads, slot-key structures, locking nuts, and the like. Carriage 72 is thereby mounted securely onto chamber 10, and duct 38 (not shown) is aligned with outlet 18. After needle 30 has been used, carriage 72 is screwed off and disposed. This embodiment saves materials and costs of manufacturing.

In the embodiment shown in FIG. 12, carriage 72 is mounted to the fluid chamber 10 by positioning spout 76 in the mounting ring or socket 70 on the chamber 10. The spout 76 and socket 70 are formed with cooperating engagement means suitable for securing the two members together such as screw threads, snap beads, slot-key structures, locking nuts, and the like. The back surface of needle carriage 72 is shaped to engage a locking mount 80 carried by the fluid chamber 10 to prevent rotational movement of the needle carriage 72 relative to the chamber 10 during insertion of the needle 30. In the illustrated embodiment, the protruding bead 82 on the locking mount 80 seats in a pocket 84 formed in the back surface of the needle carriage 72. However, it should be understood that the position of the bead 82 and the pocket 84 may be reversed. Moreover, other suitable engagement means may be used to anchor the needle carriage 72 to the locking mount 80.

A U-shaped sheath 85 is slidably mounted to the needle carriage 72. After the needle has been used, the sheath 85 slides along the carriage 72 and across the needle 30 until the contaminated tip of the needle is positioned within the sheath. Unlike the needle assemblies of the prior art, mounting the needle carriage to the side of chamber 10 allows the sheath to be sheath 85 is separate from the chamber 10, providing greater flexibility in the size of the sheath 85 and the overall assembly.

FIG. 13 shows another embodiment of the invention in which the needle carriage 72 is mounted to the fluid chamber 10 through the inter-engagement of a mounting ring or socket 70 and a spout 76. The mounting ring 70 is indexed to interlock with the spout 76 on the carriage and securely retain the needle in several different positions. As is shown in FIG. 13, the needle 30 may be held in several positions such as parallel to the longitudinal axis of the chamber 10, perpendicular to the chamber 10 or at any other angle. Orienting the needle 30 at an angle relative to the axis of the chamber 10 allows pressure to be placed on the chamber 10 during use of the assembly, when extracting Mood for example, without forcing the needle further into the patient. Various means may be used to secure the spout 76 and indexed mounting ring 70 together. For example, the mounting ring 70 may include a slot-key structure configured to permit rotation of the socket between two or more interlocked positions. In another example, the socket may be formed with a button which projects through a hole formed in the mounting ring 70 to lock the needle carriage in the desired position. By depressing the button, the button may be released and the spout rotated to bring the button into engagement with another hole formed in the mounting ring. In addition, other suitable means may be used for interlocking the spout and the mounting ring in one of several different positions.

In the embodiments shown in FIGS. 11–13, the mounting ring or socket 70 is provided on the fluid chamber 10 while the spout 76 is positioned on the needle carriage 72. However, it should be understood that in other modifications the needle carriage 72 may have the mounting ring 70 while the fluid chamber 10 may be formed with the spout.

While the above description contains many specificities, these should not be construed as limitations on the scope of the invention, but rather as an exemplification of particular embodiments thereof. Many other variations are possible. For example, the check valve can be replaced with a slide gate, or with any other mechanism which synchronizes the opening of an outlet for fluid with the presence of an external duct to receive the fluid; another alternative is a film covering which is penetrated once the outlet contacts the external duct. In fact, because of the presence of the plunger, fluid will not flow unless the plunger is pushed or pulled, so the check valve may be even unnecessary. Another variation is a different mechanism for locking the carriage. For example, the legs could jut into notches in the lateral slots, or notches in the side wall, rather than notches in the walls of the recess. The actuator buttons may be replaced by one button on the top which controls one leg. In fact, any locking mechanism can be used which locks a sliding carriage to a track based on the position of the carriage within the track, such as a retracting pen mechanism. Similarly, the tabs which prevent the carriage from sliding out once the carriage attains the "disposal-position" may be any mechanism which allows unidirectional sliding of an object within a track.

Therefore, the scope of the invention should be determined, not by the examples given, but by the appended claims and their legal equivalents.

What is claimed is:

1. A hypodermic needle assembly for use with an injection device having a fluid chamber having an outer wall and a drive means carried by said fluid chamber for creating negative pressures to cause uptake of a fluid into said fluid chamber and for creating positive pressures to cause ejection of a fluid from said fluid chamber, said needle assembly comprising:

a sheath carried by to an outer wall of a fluid chamber having a front end and a passageway extending inwardly from said front end of said sheath;

a needle carriage positioned in said sheath and having a hypodermic needle mounted thereto, said needle carriage being movable along said passageway between a forward position with said hypodermic needle projecting from said front end of said sheath and a retracted position with said hypodermic needle positioned inside of said sheath;

said sheath having a plurality of first locking members and said needle carriage having at least one second locking member cooperable with said first locking members for selectively retaining said needle carriage in each of said forward position and said retracted position when said second locking member and one of said first locking members are engaged and for moving said needle carriage relative to said sheath when said second locking member and said first locking members are disengaged, at least one of said first locking members being positioned to engage said second locking member and retain said needle carriage in a stand-by position between said forward position and said retracted position.

2. The needle of claim 1 wherein said needle carriage has two of said second locking members, said second locking members being deformable between a first position with said second locking members extending outwardly from said needle carriage to engage said first locking members and a second position with said second locking members deformed inwardly relative to said first locking members to disengage said second locking members from said first locking members.

3. The needle of claim 1 wherein said second locking member is an outward extending leg carried by said needle carriage and at least one of said first locking members is a notch formed said interior wall of said sheath.

4. The needle assembly of claim 1 wherein said second locking member is an outward extending leg carried by said needle carriage and at least one of said first locking members is a tab extending inwardly into said passageway from said interior wall of said sheath.

5. The needle assembly of claim 1 wherein said sheath has first and second slots formed therein and said first and second actuators each extend through one of said slots for guiding movement of said needle carriage along said passageway.

6. The needle assembly of claim 1 wherein said needle carriage has an internal conduit having a first end in fluid communication with said fluid chamber and a second end in fluid communication with said hypodermic needle.

7. An injection device comprising:

a syringe body having an outer wall, a fluid chamber formed therein having a longitudinal axis, and drive means carried by said syringe body for creating negative pressures to cause uptake of a fluid into said fluid chamber and for creating positive pressures to cause ejection of a fluid from said fluid chamber;

a sheath carried by said syringe body and having a front end and a recess extending inwardly from said front end of said sheath, said recess having a second longitudinal axis spaced from said first longitudinal axis of said chamber;

a needle carriage position in said sheath and having a hypodermic needle mounted thereto, said needle carriage being movable along said recess between a forward position with said hypodermic needle projecting from said front end of said sheath and a retracted position with said hypodermic needle positioned inside of said sheath;

said sheath having a plurality of first locking members and said needle carriage having at least one second locking member cooperable with said first locking members for selectively retaining said needle carriage in each of said forward position and said retracted position when said second locking member and one of said first locking members are engaged and for moving said needle carriage relative to said sheath when said second locking member and said first locking members are disengaged, at least one of said first locking members being positioned to engage said second locking member and retain said needle carriage in a stand-by position between said forward position and said retracted position.

8. The injection device of claim 7 wherein said needle carriage has two of said second locking members, said second locking members being deformable between a first position with said second locking members extending outwardly from said needle carriage to engage said first locking members and a second position with said second locking members deformed inwardly relative to said first locking members to disengage said second locking members from said first locking members.

9. The injection device of claim 7 wherein said second locking member is an outward extending leg carried by said needle carriage and at least one of said first locking members is a notch formed said interior wall of said sheath.

10. The injection device of claim 7 wherein said second locking member is an outward extending leg carded by said needle carriage and at least one of said first locking members is a tab extending inwardly into said passageway from said interior wall of said sheath.

11. The injection device of claim 7, and further comprising an actuator associated with said second locking member for movement of said second locking member between a first position engaging one of said first locking members and a second position disengaged from said first locking members, said sheath having at least one slot formed therein and said actuator extending through said slot for guiding movement of said needle carriage along said recess.

12. The injection device of claim 7 wherein said needle carriage has an internal conduit having a first end in fluid communication with said fluid chamber and a second end in fluid communication with said hypodermic needle.

13. An injection device comprising:

a syringe body having an outer wall, a fluid chamber formed therein having a longitudinal axis, and drive means carried by said syringe body for creating negative pressures to cause uptake of a fluid into said fluid chamber and for creating positive pressures to cause ejection of a fluid from said fluid chamber;

a sheath carried by said syringe body and having a front end and a recess extending inwardly: from said front end of said sheath, said recess having a second longitudinal axis spaced from said first longitudinal axis of said chamber;

a needle carriage positioned in said sheath and having a hypodermic needle mounted thereto, said needle carriage being movable along said recess between a forward position with said hypodermic needle projecting from said front end of said sheath and a retracted position with said hypodermic needle positioned inside of said sheath, said needle carriage having an internal conduit having a first end in fluid communication with said fluid chamber and a second end in fluid communication with said hypodermic needle:

said sheath having a plurality of first locking members and said needle carriage having at least one second locking member cooperable with said first locking members for selectively retaining said needle carriage in each of said forward position and said retracted position when said second locking member and one of said first locking members are engaged and for moving said needle carriage relative to said sheath when said second locking member and said first locking members are disengaged, said syringe body having a flow-control valve for controlling the flow of fluid into and out of said fluid chamber, said flow-control valve being opened when said first end of said internal conduit is substantially aligned with said flow-control valve and closed when said first end of said internal conduit is spaced from said flow-control valve.

* * * * *